(12) United States Patent
Lee et al.

(10) Patent No.: US 7,754,881 B2
(45) Date of Patent: Jul. 13, 2010

(54) AROMATIC IMIDE-BASED DISPERSANT FOR CARBON NANOTUBES AND CARBON NANOTUBE COMPOSITION COMPRISING THE SAME

(75) Inventors: Hyo Sug Lee, Suwon-si (KR); Jae Young Choi, Suwon-si (KR); Seon Mi Yoon, Yongin-si (KR); Hyuk Soon Choi, Seongnam-si (KR); Kwang Hee Kim, Seoul (KR)

(73) Assignee: Samsung Electronics Co., Ltd. (KR)

( * ) Notice: Subject to any disclaimer, the term of this patent is extended or adjusted under 35 U.S.C. 154(b) by 823 days.

(21) Appl. No.: 11/562,208

(22) Filed: Nov. 21, 2006

(65) Prior Publication Data

US 2007/0221913 A1 Sep. 27, 2007

(30) Foreign Application Priority Data

Jan. 23, 2006 (KR) .................... 10-2006-0006852

(51) Int. Cl.
*C07D 471/02* (2006.01)
*H01B 1/12* (2006.01)

(52) U.S. Cl. .................... 546/37; 252/500; 313/498

(58) Field of Classification Search .............. 546/37; 313/498; 252/500

See application file for complete search history.

(56) References Cited

U.S. PATENT DOCUMENTS 5,264,034 A 11/1993 Dietz et al.

FOREIGN PATENT DOCUMENTS

| JP | 11286489 | 10/1999 |
|---|---|---|
| KR | 1020010102598 | 11/2001 |
| KR | 1020030086442 | 11/2003 |
| KR | 1020050097711 | 10/2005 |

OTHER PUBLICATIONS

Phys. Rev. B46, 1804 (1992).
Phys. Rev. Lett. 68, 1579 (1992).

*Primary Examiner*—Charanjit S Aulakh
(74) *Attorney, Agent, or Firm*—Cantor Colburn LLP

(57) ABSTRACT

Disclosed herein are an aromatic imide-based dispersant for CNTs and a carbon nanotube composition comprising the same. Having an aromatic ring structure advantageously realizing adsorption on carbon nanotubes, the dispersant, even if used in a small amount, can disperse a large quantity of carbon nanotubes.

17 Claims, 5 Drawing Sheets

AROMATIC IMIDE-BASED DISPERSANT FOR CARBON NANOTUBES AND CARBON NANOTUBE COMPOSITION COMPRISING THE SAME

This non-provisional application claims priority to Korean Patent Application No. 10-2006-0006852, filed on Jan. 23, 2006, and all the benefits accruing therefrom under 35 U.S.C. §119(a), the disclosure of which is herein incorporated by reference in its entirety.

BACKGROUND OF THE INVENTION

1. Field of the Invention

The present invention relates to an aromatic imide-based dispersant for carbon nanotubes and a carbon nanotube composition comprising the same. More particularly, the present invention relates to an aromatic imide-based dispersant having a heterocyclic ring which is readily adsorbed on the surface of carbon nanotubes to prevent the aggregation of the carbon nanotubes and thus improve the dispersibility of the carbon nanotubes, and a nanotube composition comprising the same.

2. Description of the Related Art

Since their discovery by Dr. Sumio Iijima in 1991, carbon nanotubes ("CNT"), which are materials having a nanometer-scale size ("nano-size") have been much studied. A CNT is a honeycomb lattice of carbon atoms rolled into a cylinder, in which one carbon atom is connected with others in a hexagonal pattern. The hexagonal patterns may be interspersed with pentagonal shapes which can impart a chiral pattern to the hexagonal lattice. Having a diameter on the order of a few nanometers, a CNT exhibits characteristic electrochemical properties.

It is known that the electrical properties of CNT are determined as a function of structure and diameter (Phys. Rev. B46, 1804 (1992); Phys. Rev. Lett. 68, 1579 (1992)). Depending on the structure of a CNT and its diameter, it can behave either as an insulator, a semiconductor or a metal. For example, when the motion of free electrons is changed in CNT by modifying the spin or chirality of the CNT, the free electrons either freely move therein, thereby transforming the CNT into a conductor, or encounter a barrier to flow, thereby transforming the CNT into a semiconductor.

Thanks to superiority in mechanical strength and chemical stability, changeability between semiconductive and conductive properties, and structural characteristics of narrow, long, and hollow tubes, CNTs are highly useful when applied to nano-size electronic elements, including flat display devices, transistors, and the like, as well as to energy storage devices.

When used to form electroconductive films or in the fabrication of various electronic devices, CNTs need to be effectively dispersed in matrices such as solutions or binders. However, CNTs show great tendency to aggregate into bundles in a matrix owing to Van der Waals force, and thus the solubility of the nanotubes in water or other solvents decreases, resulting in processing difficulty.

When aggregated in a matrix rather than dispersed, carbon nanotubes cannot exhibit characteristic useful properties and/or cannot be formed into a film which has uniform properties throughout.

This strong tendency toward aggregation makes it difficult to adequately disperse CNTs in a matrix with conventional commercially available dispersants. Extensive attempts have been made to develop novel dispersants or methods for uniformly dispersing CNTs in solvents or binders.

For instance, Korean Patent Laid-Open Publication No. 2001-102598 discloses a method of introducing an alkyl group into a CNT by a chemical linkage. An alkyl group having 8 or more carbon atoms can increase the solubility of CNTs in organic solvents to hundreds of ppm by weight, but also increases the insulative properties, thereby decreasing electroconductivity. One the other hand, a smaller alkyl group cannot adequately increase the solubility of the CNT to the desired extent while maintaining electroconductivity.

Korean Patent Laid-Open Publication No. 2003-86442 discloses a method of wrapping CNTs with a polymer which is physically interactive with the nanotubes, thereby increasing the solubility thereof. However, the CNTs wrapped with the polymer are disconnected with each other so that the electroconductivity decreases. Further, in the absence of a perfect coating, the polymers as well as the carbon nanotubes can aggregate, leading to a decrease in the efficiency of the dispersant.

In Korean Patent Laid-Open Publication No. 2005-97711, a functional group selected from among cyanate, amine, hydroxy, carboxyl, halide, nitrate, thiocyanate, thiosulfate, vinyl, and combinations thereof is attached to CNTs. This method, however, injures the surface of carbon nanotubes and thereby degrades the electrical properties thereof.

Japanese Patent Laid-Open Publication No. 11-286489 discloses a pherylene compound which has improved coloristic and Theological properties, and a pigment preparation. U.S. Pat. No. 5,264,034 also discloses a pigment preparation based on a pherylene compound. However, neither coloristic pherylene pigment, addresses improved dispersibility of CNTs.

BRIEF SUMMARY OF THE INVENTION

Accordingly, the present invention has been made keeping in mind the above problems occurring in the prior art, and in an embodiments dispersant for CNTs is provided, which can prevent the aggregation of CNTs and thus improve the dispersibility of carbon nanotubes in a matrix.

in another embodiment, a carbon nanotube composition is provided in which carbon nanotubes are well dispersed, thereby assuring exhibition of their properties.

In order to accomplish the above, in an embodiment, an aromatic imide-based dispersant for CNTs is selected from the group consisting of compounds represented by the following Chemical Formulae 1 to 4:

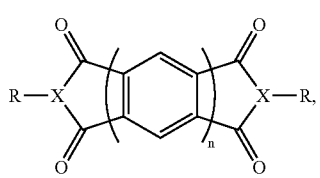

Chemical Formula 1

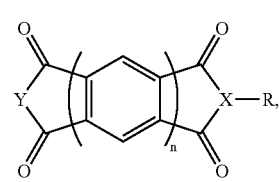

Chemical Formula 2

Chemical Formula 3

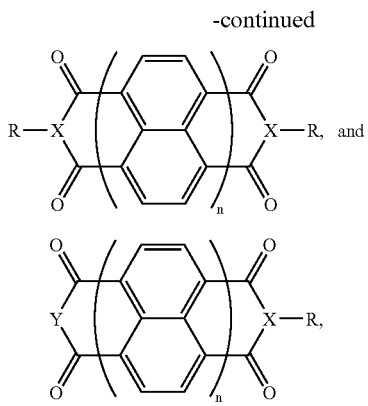

Chemical Formula 4 wherein,
X is N,
Y is O or S,

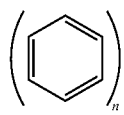

is a monocyclic or polycyclic aromatic group selected from

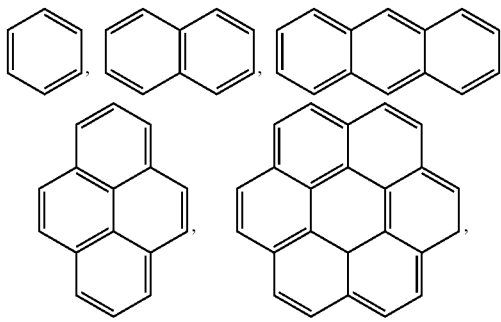

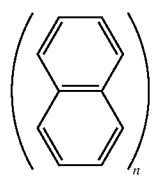

is a polycyclic aromatic group selected from 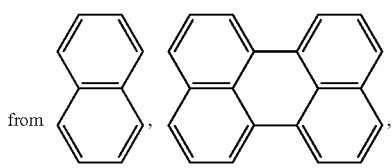 , 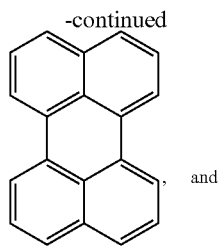 , and

R is selected from the group consisting of polymethylmethacrylate, polybutylacrylate, polyacrylic acid, polymethacrylic acid, a copolymer of polyalkylmethacrylate and polymethacrylic acid, polyoxyethylene, polyoxypropylene, polyvinylalcohol, and polyacrylamide.

In accordance with another embodiment, a carbon nanotube composition comprises an aromatic imide-based dispersant, a CNT, and a solvent.

In accordance with another embodiment, a carbon nanotube film comprises a carbon nanotube, and an aromatic imide-based dispersant.

In accordance with another embodiment, a method of preparing a carbon nanotube film comprises dispersing a carbon nanotube in a solvent with an aromatic imide-based dispersant to form a carbon nanotube composition, and coating the carbon nanotube composition on a substrate.

BRIEF DESCRIPTION OF THE DRAWINGS

The above and other features and advantages of the present invention will be more clearly understood from the following detailed description taken in conjunction with the accompanying drawings, in which.

DETAILED DESCRIPTION OF THE INVENTION

Figure 1:
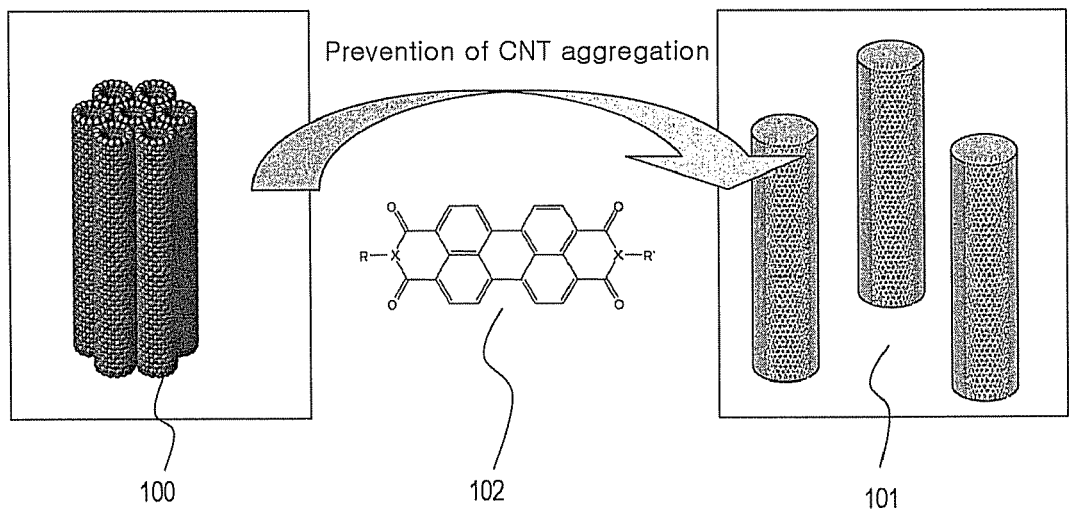
FIG. 1 is a schematic view of the operation of an exemplary dispersant.

Below, a detailed description is given of the present invention with reference to the accompanying drawings.

It will be understood in the following disclosure of the present invention, that as used herein, the singular forms "a", "an" and "the" are intended to include the plural forms as well, unless the context clearly indicates otherwise. It will be further understood that the terms "comprise", "comprises", and "comprising," when used in this specification, specify the presence of stated features, integers, steps, operations, elements, components, and combination of the foregoing, but do not preclude the presence and/or addition of one or more other features, integers, steps, operations, elements, components, groups, and combination of the foregoing.

It will be understood that when an element is referred to as being "on" another element, or when an element is referred to as being "disposed between" two or more other elements, it can be directly on (i.e., in at least partial contact with) the other element(s), or an intervening element or elements may be present therebetween. In contrast, when an element is referred to as being "disposed on" another element, the elements are understood to be in at least partial contact with each other, unless otherwise specified. Spatially relative terms, such as "between", "in between" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. The device may be otherwise oriented (rotated 90 degrees, inverted, or at other orientations) and the spatially relative descriptors used herein interpreted accordingly.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The aromatic imide-based dispersant has one of the structures represented by the following Chemical Formulae 1 to 4:

Chemical Formula 1
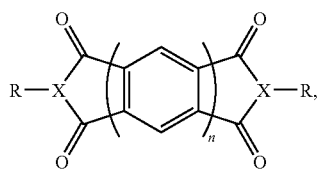

Chemical Formula 2
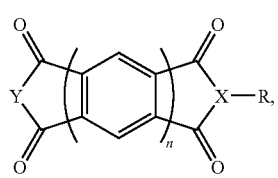

Chemical Formula 3
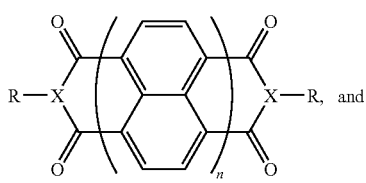

Chemical Formula 4
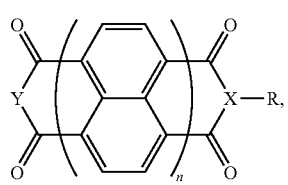

wherein,
X is N
Y is O or S,

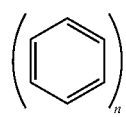

is a monocyclic or polycyclic aromatic group selected from

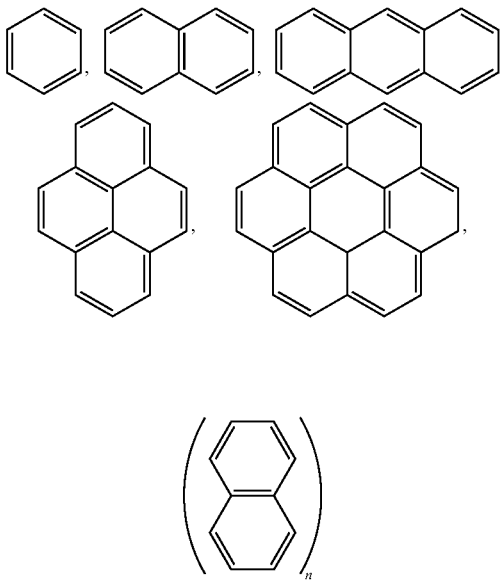

is a polycyclic aromatic group selected from

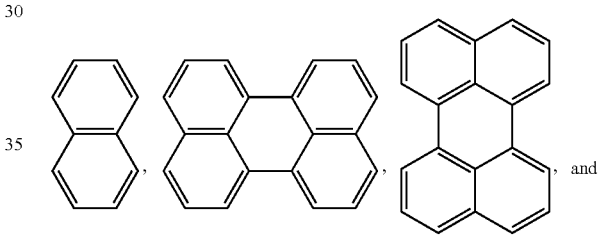
, and

R is selected from the group consisting of polymethylmethacrylate, polybutylacrylate, polyacrylic acid, polymethacrylic acid, a copolymer of polyalkylmethacrylate and polymethacrylic acid, polyoxyethylene, polyoxypropylene, polyvinylalcohol, and polyacrylamide.

A CNT has π electrons on the surface thereof. Because the dispersant is a heterocyclic ring structure that is readily coupled with CNTs through π-π interaction, it can be adsorbed on CNTs, thereby dispersing them in matrices. That is, if the π-π interaction between a dispersant and a CNT is stronger than that between CNTs, the dispersant breaks up aggregates of CNTs and thus scatters (i.e., disperses) CNTs individually.

Generally, however, there is a weak π-π interaction between a CNT and a dispersant. When a π-π interaction between a dispersant and CNT does not significantly differ from that between CNTs, the dispersant exerts only limited dispersibility on CNTs.

As for an n-type semiconductor, its structure consists of aromatic rings that can form π-π interactions. When such an n-type semiconductor is adsorbed on a CNT, charge transfer occurs from the CNT to the n-type semiconductor, generating a certain quantity of positive charge in the CNT. The orbital hybridization of the CNT delocalizes the positive charge over the surface of the CNT. Accordingly, the delocalized positive charge causes electrostatic repulsion between the CNTs (repulsive force between positively charged CNTs). In addition, having an amine group capable of bonding with a carboxyl group, which is a functional group reactive to CNTs, the dispersant has high affinity for CNTs.

Referring to FIG. 1, the dispersant 102 prevents (i.e., restrains) CNTs from aggregating in a solvent, and can break up aggregated CNTs 100 into dispersed CNTs 101. In this way, CNTs can be solubilized at a high concentration in the solvent without degrading electrical, physical, and other properties of the CNTs, such as electroconductivity.

Figure 2:
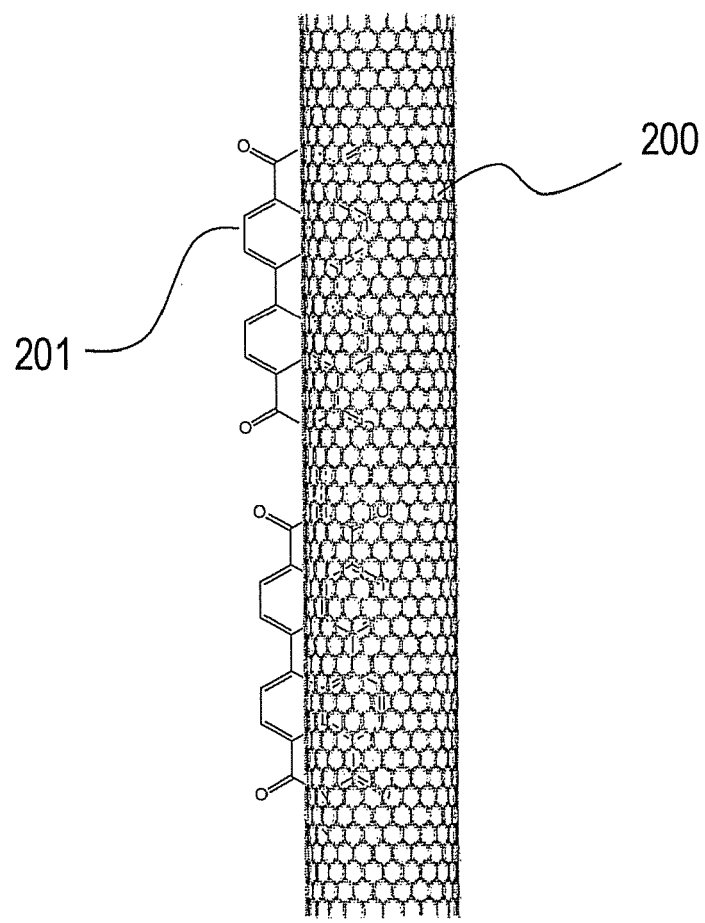
FIG. 2 is a schematic view showing a CNT having a dispersant adsorbed thereon.

FIG. 2 shows a CNT 200 with the aromatic imide-based dispersant 201 of the present invention adsorbed thereon. The adsorption of the aromatic imide-based dispersant 201 onto CNT 200 results from a π-π interaction therebetween, which leads to the solubilization of the CNT.

Examples of the aromatic imide-based dispersant useful in the present invention include compounds represented by the following Chemical Formulae 5 to 8:

Chemical Formula 5

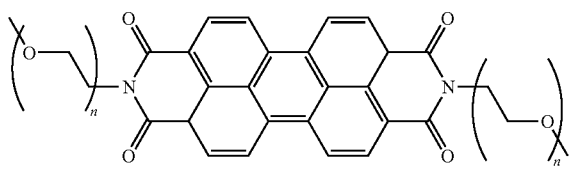

wherein n is an integer from 4 to 15;

Chemical Formula 6

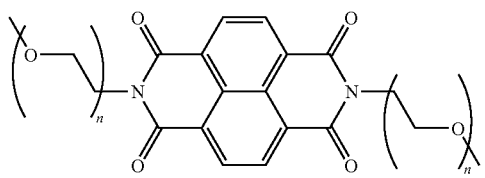

wherein n is an integer from 4 to 15;

Chemical Formula 7

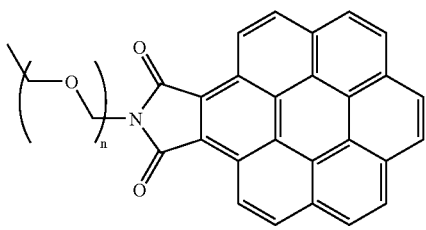

wherein n is an integer from 4 to 15; and

Chemical Formula 8

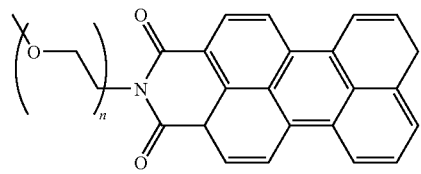

wherein n is an integer from 4 to 15.

The aromatic imide-based dispersant can be synthesized as follows. In an embodiment, an alkyl chain having a terminal OH group ("ROH") is converted to a leaving group by treatment with a sulfonyl chloride and displaced with a —CN group ("RCN") or —N₃ group ("RN₃") which is then converted to —NH₂ to form the amine-terminated chain RNH₂. This chain is reacted with an aromatic carboxyl anhydride to form an imide as shown in Reaction Formula 1.

Reaction Formula 1

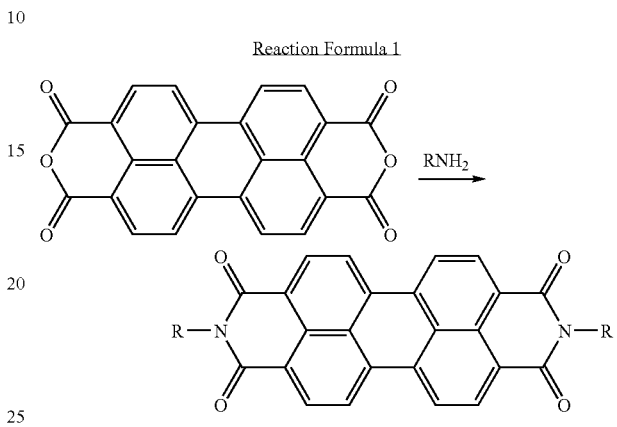

In another embodiment, a carbon nanotube composition includes the aromatic imide-based dispersant. The carbon nanotube composition thus comprises a carbon nanotube, the aromatic imide-based dispersant, and a solvent. Carbon nanotube films prepared from the carbon nanotube composition, in which the carbon nanotubes are uniformly dissolved in the solvent with the aid of the aromatic imide-based dispersant, can find a broad variety of applications including transparent conductive films, organic solar cells, electrode materials for batteries, and the like.

The carbon nanotube composition comprises the aromatic imide-based dispersant in an amount of 0.001 to 10 wt %; a carbon nanotube in an amount from 0.01 to 5 wt %; and a solvent, based on the total weight of carbon nanotube, aromatic imide-based dispersant, and solvent. In and embodiment, in the carbon nanotube composition, the carbon nanotube is mixed in a weight ratio of 1:0.001 to 1:10 with the aromatic imide-based dispersant. The carbon nanotube composition may optionally comprise a binder and/or other organic additives, present in an amount such that the desired properties of a carbon nanotube film prepared therefrom are not substantially adversely affected.

Different types of carbon nanotubes are useful for the carbon nanotube composition. In an embodiment, the carbon nanotube contained in the carbon nanotube composition may be selected from: a single wall carbon nanotube, a double-wall carbon nanotube, a triple-wall carbon nanotube, a quadruple-wall carbon nanotube, a carbon nanohorn, a carbon nanofiber, and combinations thereof. It will be understood that useful carbon nanotubes are exemplified by, but are not limited to, the foregoing list of carbon nanotubes.

Exemplary solvents useful in the carbon nanotube composition include aqueous based solvents including water; alcohols, such as methanol, ethanol, isopropyl alcohol, propyl alcohol, butanol, terpineol, and the like; ketones, such as acetone, methylethyl ketone, ethyl isobutyl ketone, methyl isobutyl ketone and the like; ethyleneglycols, such as ethyleneglycol, ethyleneglycol methylether, ethyleneglycol mono-n-propylether, and the like; propyleneglycols, such as propyleneglycol, propyleneglycol methylether, propyleneglycol ethylether, propyleneglycol butylether, propyleneglycol propylether, and the like; amides, such as dimethylformamide, dimethylacetamide, and the like; pyrrolidones, such as N-methyl-2-pyrrolidone ("NMP"), N-ethylpyrrolidone and the like; hydroxyesters, such as lactic acid methyl ester, lactic acid ethyl ester, β-methoxyisobutyric acid methyl ester, α-hydroxyisobutyric acid methyl ester and the like; sulfoxides such as dimethylsulfoxide; lactones such as γ-butyrolactone; anilines, such as aniline, N-methylaniline and the like; hydrocarbons such as hexane; halogenated solvents such as chloroform; aromatic solvents such as toluene; and glycol esters such as propylene glycol monomethyl ether acetate ("PGMEA"); and a combination comprising at least one of the foregoing solvents, but are not limited thereto.

Using a mixing or a kneading apparatus, such as an ultrasonicator, a homogenator, a spiral mixer, a planetary mixer, a disperser, a blending mixer, or the like, the carbon nanotube and the dispersant may be dispersed by mixing in the solvent to prepare the carbon nanotube composition.

The carbon nanotube composition can disperse the carbon nanotubes in a matrix, such as in a solution or a binder, without degrading (i.e., significantly adversely affecting) the electrical and optical properties of the carbon nanotubes themselves. The carbon nanotube composition thus enjoys the advantage of having superior conductivity, film formation, and moldability in addition to showing excellent dispersion stability, such that the carbon nanotubes are neither separated from the solvent nor aggregate for a long period of time.

A simple coating technique, such as spin coating, electrophoretic deposition, inkjet printing, or the like, may be used to apply the carbon nanotube composition to a substrate.

Thus, a carbon nanotube film comprises a carbon nanotube, and an aromatic imide-based dispersant. In addition, a method of preparing a carbon nanotube film comprises dispersing a carbon nanotube in a solvent with an aromatic imide-based dispersant, to form a carbon nanotube composition, and coating the carbon nanotube composition on a substrate. The solvent may then be removed by drying to form the carbon nanotube film.

Applications of the carbon nanotube composition may be found in preparing electronic devices including transparent electrodes for displays, such as field effect displays ("FEDs"), light emitting displays ("LEDs"), and liquid crystal displays ("LCDs"), organic transistors, wiring materials, smart cards, antennae, electrical cells, fuel cells, capacitors or inductors for printed circuit boards ("PCBs"), electromagnetic shielding films, luminescent materials, buffering materials, electron transporting materials, hole transporting materials, and the like.

A better understanding of the present invention may be realized with the following examples, which are set forth to illustrate, but are not to be considered as limited thereto.

EXAMPLES

Synthesis Example

Synthesis of Aromatic Imide-Based Dispersant

The aromatic imide-based dispersant of Chemical Formula 1 was synthesized according to the reaction scheme represented by the following Reaction Formula 2.

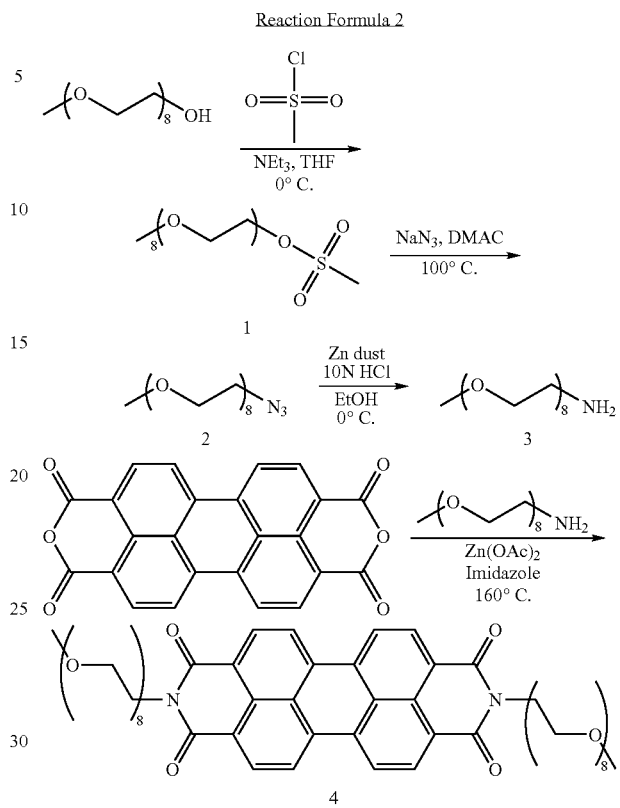

Synthesis of Compound 1

To THF (600 ml) was added poly(ethylene glycol) monomethyl ether ("PEGME", Mw=350, 70 g) and triethylamine (30.7 ml, 220 mmol) and the solution was cooled to 0° C. Methanesulfonyl chloride (17 ml, 220 mmol) was slowly added over the 1 hour period during which the reaction proceeded. After the reaction was terminated, the solution was filtered through a celite pad. The filtrate was extracted with $CH_2Cl_2$, and dried to afford Compound 1 as a yellow liquid. (85 g, Yield 95%).

Synthesis of Compound 2

To a solution of sodium azide (55.6 g, 855 mmol) in dimethyl acetamide (270 ml), Compound 1 (85 g, 190 mmol) was added dropwise over 30 min. After reacting at 100° C. for 16 hours, the solution was extracted with $CH_2Cl_2$. Vacuum removal of dimethylacetamide produced Compound 2 as a yellow liquid. (75 g, yield 96%).

Figure 3A:
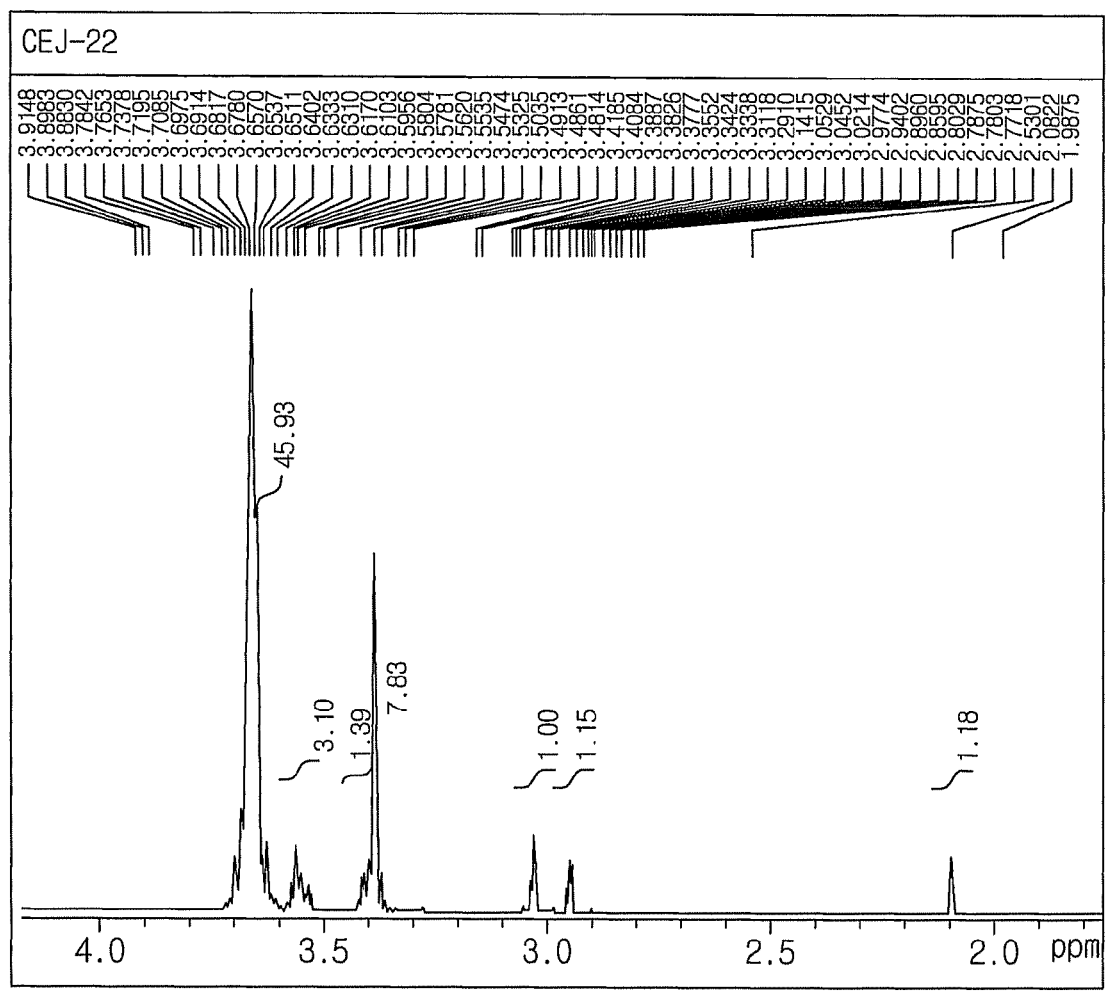
FIGS. 3*a*-3*c* are $^1$H-NMR of exemplary intermediates for the dispersant produced in the course of the synthesis of the dispersant.

$^1$H NMR (δ, $CDCl_3$): 3.38 (s, 3H), 3.49 (m, 2H), 3.6~3.7 (m, 14H). (See FIG. 3a).

Synthesis of Compound 3

To ethanol (400 ml) were added Compound 2 (75 g, 183 mmol) and Zn dust (36 g, 549 mmol) and the solution was cooled to 0° C. 10N HCl (aq) (54.9 ml) was slowly added with the temperature maintained. Reaction was conducted for 5 hours at the same temperature, followed by neutralization with NaOH (aq) and then extraction with $CH_2Cl_2$. Removal of the solvent produced Compound 3 as a yellow liquid (50 g, yield 71%).

Figure 3B:
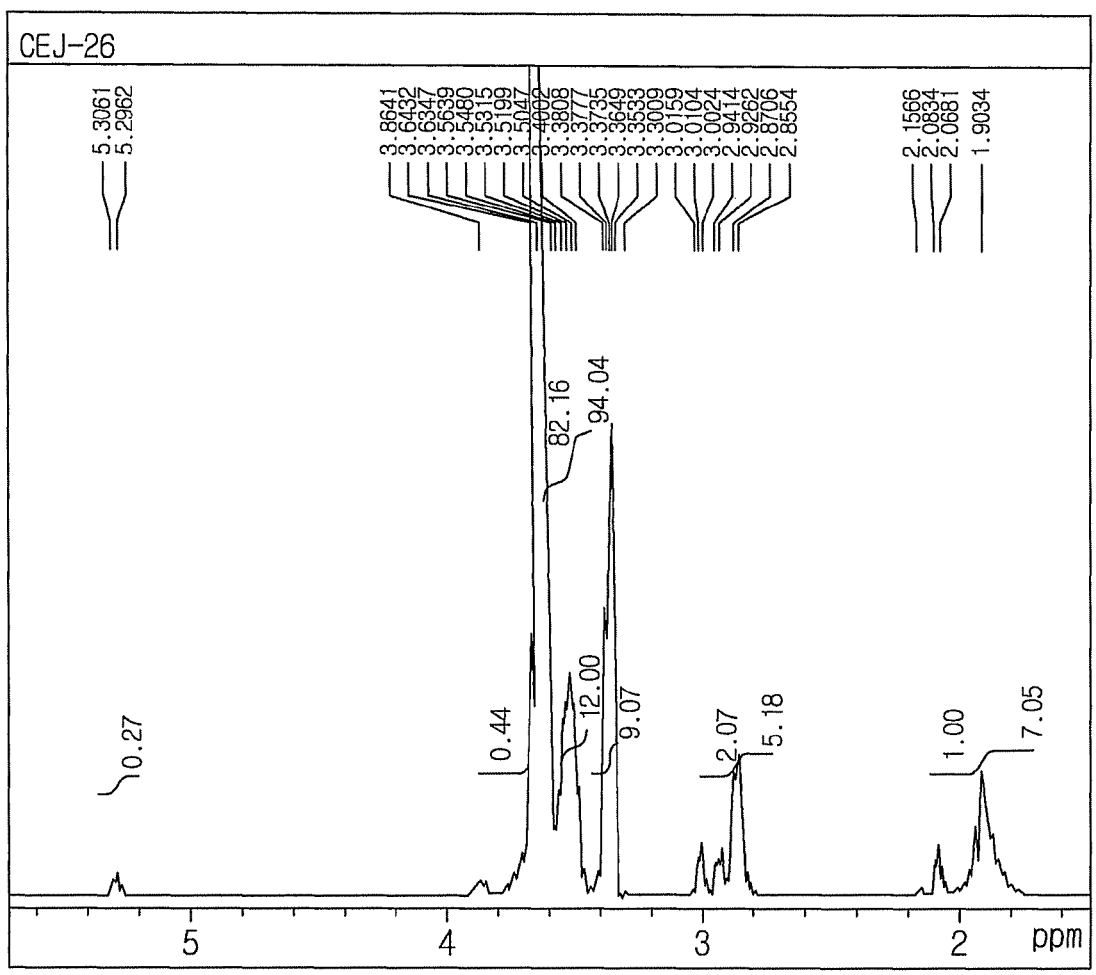

$^1$H NMR (δ, $CDCl_3$): 2.86 (m, 2H), 3.38 (s, 3H), 3.50 (m, 2H), 3.6 (m, 14H). (See FIG. 3b).

Synthesis of Compound 4

Compound 3 (15.3 g, 40 mmol), 3,4,9,10-pherylene-tetracarboxylic anhydride (4 g, 10 mmol), imidazole (1.9 g, 29 mmol), and Zn(OAc)$_2$ (0.4 g, 2.2 ml) were combined and reacted at 160° C. for 16 hours in an argon atmosphere. The reaction proceeded as the solids were melted by heat. Following reaction termination, the addition of 6N HCl(aq) (60 ml) and ethanol (60 ml) and the extraction with CH$_2$Cl$_2$ were conducted sequentially. The extract was purified by silica gel column chromatography (2% methanol in CH$_2$Cl$_2$) to afford Compound 4 as a reddish solid (9.2 g, Yield 82%).

Figure 3C:
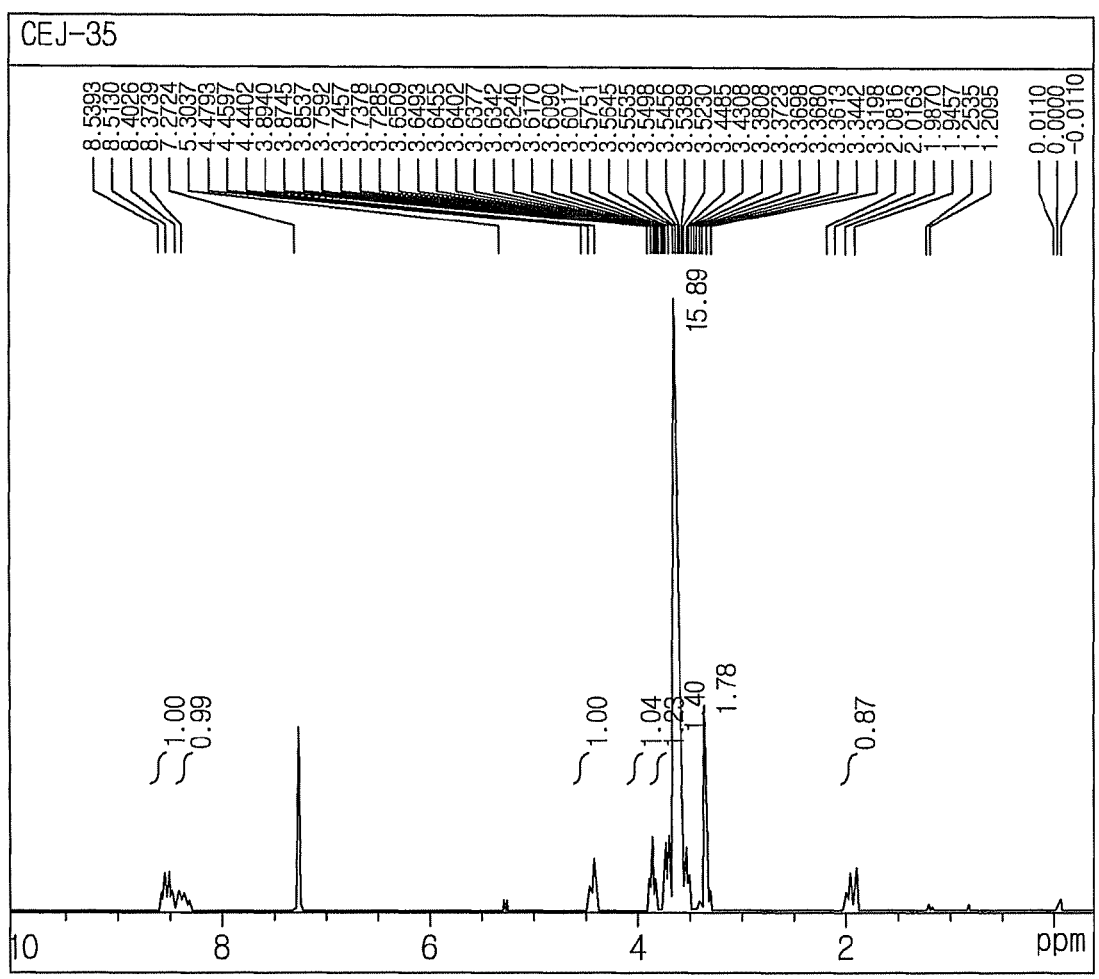

$^1$H NMR (δ, CDCl$_3$): 3.36 (m, 3H), 3.54 (m, 2H), 3.6 (m, 14H), 3.74 (m, 2H), 3.87 (t, 2H), 4.46 (t, 2H), 8.38 (d, 2H), 8.52 (d, 2H). (See FIG. 3c).

Example 1

Figure 4:
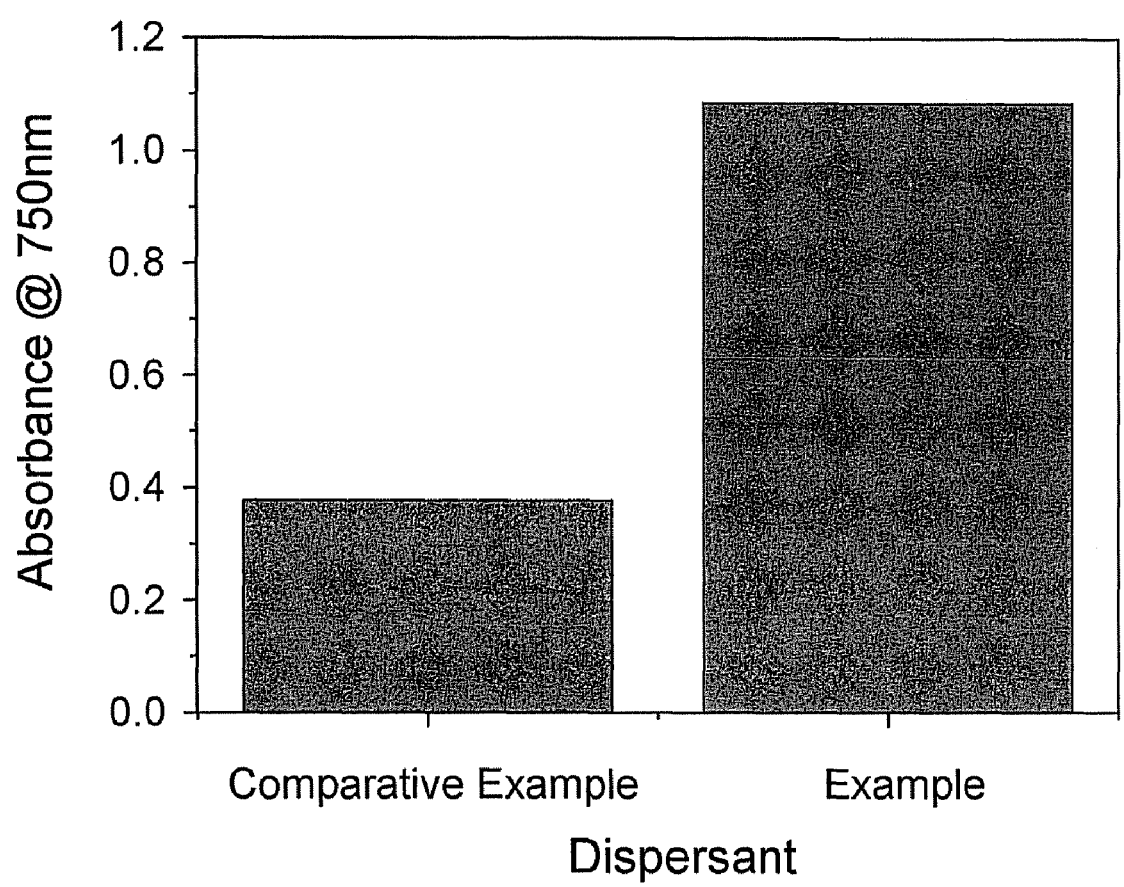
FIG. 4 is a graph showing the comparison of absorbance at 750 nm between the exemplary dispersant of Example 1 and of Comparative Example 1.

In 20 g of terpineol was dissolved 200 mg of the aromatic imide-based dispersant of Compound 4, synthesized in Synthesis Example, followed by the addition of 2 mg of a single-wall CNT to the solution. After being treated for 10 hours in a sonic bath to disperse the CNT, the solution was centrifuged at 5,000 rpm for 5 min to yield a carbon nanotube solution as a supernatant. The carbon nanotube solution was measured for absorbance at 750 nm using UV-Vis-spectroscopy (JASCO(V-560) (Absorbance mode, Scanning speed: 400 nm/min), and the results are shown in FIG. 4.

Comparative Example 1

In 20 g of terpineol was dissolved 200 mg of the dispersant of Chemical Formula 9 (shown below), and 2 mg of a single-wall carbon nanotube was added to the solution, followed by dispersing the nanotube for 13 hours in a sonic bath (35 kHz, 400 W). The solution was centrifuged at 5,000 rpm for 5 min to yield a supernatant. This was measured for absorbance at 750 nm through UV-Vis-spectroscopy (JASCO V-560) (Absorbance mode, Scanning speed: 400 nm/min) and the results are shown in FIG. 4.

Chemical Formula 9

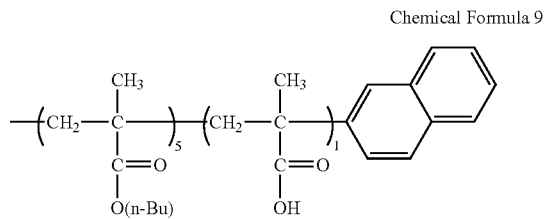

As shown in FIG. 4, a higher absorbance was realized by the aromatic imide-based dispersant of Example 1 than by the dispersant of Comparative Example 1, showing that the carbon nanotube was dispersed at a higher concentration. In detail, the aromatic imide-based dispersant disperses at 4 to 4.5-fold higher efficiency than does the conventional dispersant of Chemical Formula 9.

The aromatic imide-based dispersant for carbon nanotubes in accordance with the present invention has an aromatic ring structure which is advantageous with respect to π-π interaction with carbon nanotubes compared to conventional dispersants. Accordingly, even a small amount of the aromatic imide-based dispersant can disperse a large quantity of carbon nanotubes. In addition, the aromatic imide-based dispersant can form a composite with CNTs in a dispersed state.

Having high dispersibility, the carbon nanotube composition ensures the provision of carbon nanotubes having characteristic electrochemical properties and can be formed into a thin film having uniform properties throughout.

Although the preferred embodiments of the present invention have been disclosed for illustrative purposes, those skilled in the art will appreciate that various modifications, additions and substitutions are possible. Accordingly, the modifications, additions and substitutions should be understood as falling within the scope and spirit of the invention.

What is claimed is:

1. An aromatic imide-based dispersant for carbon nanotubes, selected from the group consisting of compounds represented by the following Chemical Formulas 3:

Chemical Formula 3

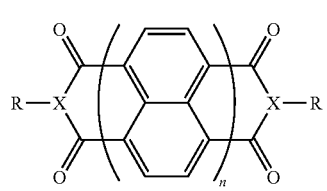

wherein,
X is N,

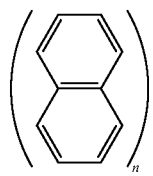

is a polycyclic aromatic group of the structure

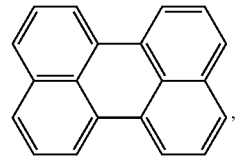

and
R is selected from the group consisting of polymethylmethacrylate, polybutylacrylate, polyacrylic acid, polymethacrylic acid, a copolymer of polyalkylmethacrylate and polymethacrylic acid, polyoxyethylene, polyoxypropylene, polyvinylalcohol, and polyacrylamide.

2. The aromatic imide-based dispersant as set forth in claim 1, wherein the aromatic imide-based dispersant is one of the compounds represented by Chemical Formula 5:

Chemical Formula 5

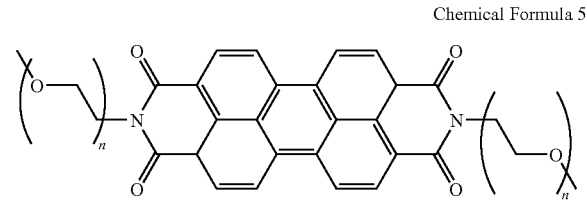

wherein n is an integer from 4 to 15.

3. A carbon nanotube composition, comprising an aromatic imide-based dispersant of claim 1, a carbon nanotube, and a solvent.

4. The carbon nanotube composition as set forth in claim 3, wherein the aromatic imide-based dispersant is one of the compounds represented by Chemical Formula 5:

Chemical Formula 5

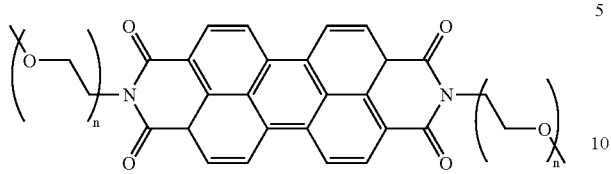

wherein n is an integer from 4 to 15.

5. The carbon nanotube composition as set forth in claim 3, wherein the composition contains the aromatic imide-based dispersant in an amount from 0.001 to 10 wt %, the carbon nanotube in an amount from 0.01 to 5 wt %, and the solvent based on the total weight of aromatic imide-based dispersant, carbon nanotube, and solvent.

6. The carbon nanotube composition as set forth in claim 3, wherein the carbon nanotube is mixed at a weight ratio of 1:0.001 to 1:10 with the aromatic imide-based dispersant.

7. The carbon nanotube composition as set forth in claim 3, wherein the carbon nanotube is selected from a group consisting of a single-wall carbon nanotube, a double-wall carbon nanotube, a triple-wall carbon nanotube, a quadruple-wall carbon nanotube, a carbon nanohorn, a carbon nanofiber, and combinations thereof.

8. The carbon nanotube composition as set forth in claim 3, wherein the solvent is selected from the group consisting of aqueous based solvents; alcohols; ketones; ethyleneglycols; propyleneglycols; amides; pyrrolidones; hydroxyesters; sulfoxides; lactones; anilines; hydrocarbons; halogenated solvents; aromatic solvents; glycol esters; and a combination comprising at least one of the foregoing solvents.

9. The carbon nanotube composition as set forth in claim 8, wherein the solvent is selected from the group consisting of water, methanol, ethanol, isopropyl alcohol, propyl alcohol, butanol, terpineol, acetone, methylethyl ketone, ethyl isobutyl ketone, methylisobutyl ketone, ethyleneglycol, ethyleneglycol methylether, ethyleneglycol mono-n-propylether, propyleneglycol, propyleneglycol methylether, propyleneglycol ethylether, propyleneglycol butylether, propyleneglycol propylether, dimethylformamide, dimethylacetoamide; N-methyl-2-pyrrolidone(NMP), N-ethylpyrrolidone, dimethylsulfoxide, γ-butyrolactone, lactic acid methyl ester, lactic acid ethyl ester, β-methoxyisobutyric acid methyl ester, and α-hydroxyisobutyric acid methyl ester, aniline, N-methylaniline, hexane; chloroform; toluene; propylene glycol monomethyl ether acetate (PGMEA) and a combination comprising at least one of the foregoing solvents.

10. A carbon nanotube film comprising a carbon nanotube, and an aromatic imide-based dispersant selected from the group consisting of compounds represented by the following Chemical Formula 3:

Chemical Formula 3

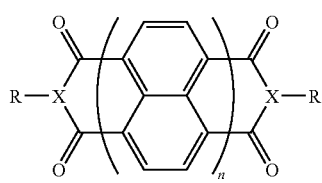

wherein,
X is N,

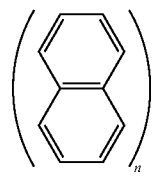

is a polycyclic aromatic group of the structure

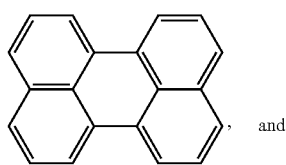, and

R is selected from the group consisting, of polymethylmethacrylate, polybutylacrylate, polyacrylic acid, polymethacrylic acid, a copolymer of polyalkylmethacrylate and polymethacrylic acid, polyoxyethylene, polyoxypropylene, polyvinylalcohol, and polyacrylamide.

11. The carbon nanotube film as set forth in claim 10, wherein the aromatic imide-based dispersant is one of the compounds represented by Chemical Formula 5:

Chemical Formula 5

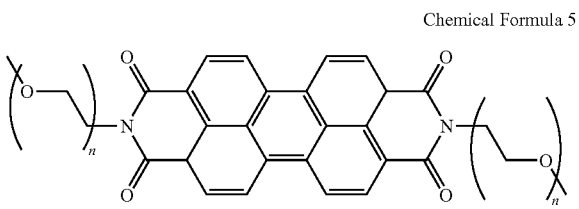

wherein n is an integer from 4 to 15.

12. An electronic device comprising the carbon nanotube film as set forth in claim 10.

13. A method of preparing a carbon nanotube film comprising:
dispersing a carbon nanotube in a solvent with an aromatic imide-based dispersant to form a carbon nanotube composition, wherein the aromatic imide-based dispersant is selected from the group consisting of compounds represented by the following Chemical Formula 3:

Chemical Formula 3

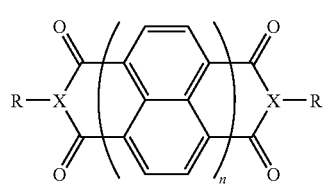

wherein,

X is N,

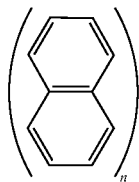

is a polycyclic aromatic group of the structure

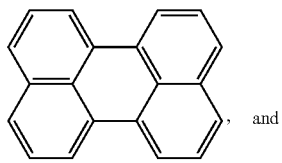, and

R is selected from the group consisting of polymethylmethacrylate, polybutylacrylate, polyacrylic acid, polymethacrylic acid, a copolymer of polyalkylmethacrylate and polymethacrylic acid, polyoxyethylene, polyoxypropylene, polyvinylalcohol, and polyacrylamide;

casting the carbon nanotube composition on a substrate.

14. The method as set forth in claim 13, wherein the aromatic imide-based dispersant is one of the compounds represented by Chemical Formula 5:

Chemical Formula 5

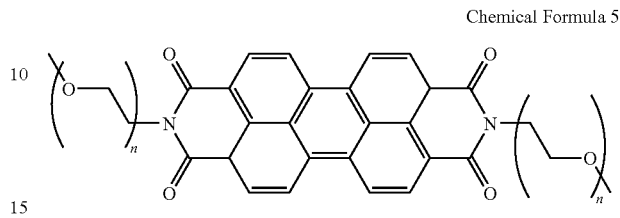

wherein n is an integer from 4 to 15.

15. The method as set forth in claim 13, wherein dispersing is accomplished by mixing using an apparatus including an ultrasonicator, a homogenator, a spiral mixer, a planetary mixer, a disperser, or a blending mixer.

16. The method as set forth in claim 13 wherein casting is accomplished using a coating technique comprising spin coating, electrophoretic deposition, or inkjet printing.

17. A carbon nanotube film prepared by the method as set forth in claim 13.

* * * * *